US006875882B2

(12) United States Patent
Chorghade et al.

(10) Patent No.: US 6,875,882 B2
(45) Date of Patent: Apr. 5, 2005

(54) SYNTHESIS OF BENZONITRILES FROM SUBSTITUTED BENZOIC ACID

(75) Inventors: Mukund S. Chorghade, Natick, MA (US); Mukund K. Gurjar, Pune Maharashtra (IN); Joseph Cherian, Kerala (IN)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 10/439,341

(22) Filed: May 15, 2003

(65) Prior Publication Data

US 2004/0002613 A1 Jan. 1, 2004

Related U.S. Application Data

(60) Provisional application No. 60/381,012, filed on May 15, 2002, provisional application No. 60/381,021, filed on May 15, 2002, provisional application No. 60/380,894, filed on May 15, 2002, provisional application No. 60/380,910, filed on May 15, 2002, provisional application No. 60/380,880, filed on May 15, 2002, provisional application No. 60/381,017, filed on May 15, 2002, provisional application No. 60/380,894, filed on May 15, 2002, provisional application No. 60/380,903, filed on May 15, 2002, provisional application No. 60/384,013, filed on May 15, 2002, provisional application No. 60/380,878, filed on May 15, 2002, provisional application No. 60/380,909, filed on May 15, 2002, and provisional application No. 60/392,833, filed on Jun. 27, 2002.

(51) Int. Cl.$^7$ ............................................ C07C 255/50
(52) U.S. Cl. .................. 558/309; 558/423; 548/237
(58) Field of Search ................................ 558/309, 473; 548/237

(56) References Cited

U.S. PATENT DOCUMENTS

| | | | |
|---|---|---|---|
| 4,406,905 A | 9/1983 | Zähner et al. | |
| 5,554,753 A | 9/1996 | O'Donnell et al. | |
| 5,840,739 A | 11/1998 | Bergeron, Jr. | |
| 5,872,259 A | 2/1999 | Reuter | |
| 5,929,232 A | 7/1999 | Jacobsen et al. | |
| 6,083,966 A | 7/2000 | Bergeron, Jr. | |
| 6,159,983 A | 12/2000 | Bergeron, Jr. | |
| 6,383,233 B1 | 5/2002 | Reuter | |
| 6,428,583 B1 | 8/2002 | Reuter | |
| 6,521,652 B1 | 2/2003 | Bergeron | |
| 6,525,080 B1 | 2/2003 | Bergeron | |
| 6,559,315 B1 | 5/2003 | Bergeron | |
| 2003/0088105 A1 | 5/2003 | Krich et al. | |
| 2003/0220504 A1 | 11/2003 | Chorghade et al. | |
| 2003/0225287 A1 | 12/2003 | Chorghade et al. | |
| 2003/0229231 A1 | 12/2003 | Chorghade et al. | |
| 2003/0236404 A1 | 12/2003 | Gimi et al. | |
| 2003/0236426 A1 | 12/2003 | Chorghade et al. | |
| 2003/0236434 A1 | 12/2003 | Gimi et al. | |
| 2003/0236435 A1 | 12/2003 | Gimi et al. | |
| 2004/0006224 A1 | 1/2004 | Chorghade et al. | |
| 2004/0024224 A1 | 2/2004 | Chorghade et al. | |
| 2004/0082796 A1 | 4/2004 | Chorghade et al. | |

FOREIGN PATENT DOCUMENTS

| | | |
|---|---|---|
| DE | 2020866 | 11/1971 |
| DE | 30 02 989 A1 | 7/1981 |
| EP | 1 302 467 A2 | 4/2003 |
| GB | 1 292 170 | 10/1972 |
| WO | WO 94/11367 | 5/1994 |
| WO | WO 97/36885 | 10/1997 |
| WO | WO 00/01670 | 1/2000 |
| WO | WO 00/12493 A1 | 3/2000 |
| WO | WO 00/16763 | 3/2000 |
| WO | WO 01/51477 A1 * | 7/2001 |

OTHER PUBLICATIONS

Bergeron, R., et al., "Desazadesmethyldesferrithiocin Analogues as Orally Effective Iron Chelators," *J. Med. Chem.*, 42:95–108 (1999).

Bergeron, R. et al., "Synthesis and Biological Evaluation of Naphthyldesferrithiocin Iron Chelators," *J. Med. Chem.*, 39:1575–1581 (1996).

Bergeron, R. et al., "Evaluation of Desferrithiocin and Its Synthetic Analogues as Orally Effective Iron Chelators," *J. Med. Chem.*, 34:2072–2078 (1991).

Bergeron, R. et al., "Evaluation of the Desferrithiocin Pharmacophore as a Vector for Hydroxamates," *J. Med. Chem.*, 42:2881–2886 (1999).

Bergeron, R. et al., "An Investigation of Desferrithiocin Metabolism," *J. Med. Chem.*, 37:2889–2895 (1994).

Bergeron, R. et al., "A Comparative Study of the Iron-Clearing Properties of Desferrithiocin Analogues with Desferrioxamine B in a *Cebus* Monkey Model," *Blood*, 81(8):2166–2173 (1993).

Bergeron, R. et al., "Pharmacokinetics of Orally Administered Desferrithiocin Analogs in *Cebus Apella* Primates," *Drug Metabolism and Disposition*, 27(12):1496–1498 (1999).

"Aliphatic Nucleophilic Substitution," In *Advanced Organic Chemistry*, by Jerry March (Wiley Interscience), Ch. 10, pp. 433–434 (1992).

(Continued)

*Primary Examiner*—Bernard Dentz
(74) *Attorney, Agent, or Firm*—Hamilton, Brook, Smith & Reynolds, PC

(57) ABSTRACT

There is a significant demand for organic nitriles, based on their versatility in reactions. Compounds prepared from nitriles have properties including superoxide inhibition, ferrielectric liquid crystal dopant, antipicornaviral agents, anti-inflammatory agents, anti-asthma agents, and fibringoen antagonists. The present invention discloses a facile synthesis for 2,4-dihydroxybenzonitrile, and ethers and diethers thereof, from 2,4-dihydroxybenzoic acid. The present invention also discloses a method of preparing a class of iron chelating agents related to desferrithiocin, all of which contain a thiazoline ring. In this method, 2,4-dihydroxybenzonitrile is condensed with (S)-2-methylcysteine.

13 Claims, No Drawings

OTHER PUBLICATIONS

"Eliminations," In *Advanced Organic Chemistry*, by Jerry March (Wiley Interscience), Ch. 17, pp. 1012–1014 (1992).

Mulqueen, G. C., et al., "Synthesis of the Thiazoline–based Siderophore (S)–Desferrithiocin," *Tetrahedron*, 49(24):5359–5364 (1993).

O'Donnell, M.J., et al., "α–Methyl Amino Acids by Catalytic Phase–Transfer Aklylations," *Tetrahedron Letters*, 23(41):4259–4262 (1982).

House, Herbert O., "*Modern Synthetic Reactions*," $2^{nd}$ edition, W. A. Benjamin, Inc., London, pp. 546–547 (1972).

Bergeron, R.J., et al., "The Desferrithiocin Pharmacophore," *J. Med. Chem.*, 37: 1411–1417 (1994).

Bergeron, R.J., et al., "Effects of C–4 Stereochemistry and C–4' Hydroxylation on the Iron Clearing Efficiency and Toxicity of Desferrithiocin Analogues," *J. Med. Chem., 42*: 2432–2440 (1999).

\* cited by examiner

SYNTHESIS OF BENZONITRILES FROM SUBSTITUTED BENZOIC ACID

RELATED APPLICATIONS

This application claims the benefit of U.S. Provisional Application Nos. 60/381,012, 60/381,021, 60/380,894, 60/380,910, 60/380,880, 60/381,017, 60/380,895, 60/380,903, 60/381,013, 60/380,878 and 60/380,909, all of which were filed May 15, 2002. This application also claims the benefit of U.S. Provisional Application No. 60/392,833, filed Jun. 27, 2002. The entire teachings of the above-referenced applications are incorporated herein by reference.

BACKGROUND OF THE INVENTION

Nitrile-containing compounds are highly in demand because nitrile moieties are versatile reagents for organic synthesis, as exemplified in their applications in the preparation of thiazoles, chrial 2-oxazolines, tetrazoles, 1,2-diarylimidazoles, triazolo[1,5-c]pyrimidines, and benzamidines. Compounds prepared from nitriles have properties including superoxide inhibition, ferrielectric liquid crystal dopants, antipicornaviral agents, anti-inflammatory agents, anti-asthma agents, and fibrinogen antagonists.

The use of nitriles in the preparation of thiazoles, or when reduced, thiazolines and thiazolidines, is of particular interest. Compounds such as desferrithiocin and structural analogues contain a thiazoline ring, and these compounds represent an advance in iron chelation therapy for subjects suffering from iron overload diseases. Present therapeutic agents such as desferroxamine require parenteral administration and have a very short half-life in the body, so that patient compliance and treatment cost are serious problems for subjects receiving long-term chelation therapy. Desferrithiocin and related compounds are effective when orally administered, thereby reducing patient compliance issues.

Unfortunately, 2,4-dihydroxybenzonitrile, which is a precursor to the potent, less toxic form of desferrithiocin known as 4'-hydroxydesazadesferrithiocin, remains a synthetic challenge. At this time, 2,4-dihydroxybenzonitrile is not commercially available and the related 2,4-dimethoxybenzonitrile is expensive. Therefore, there is a need for novel methods of producing 2,4-dihydroxybenzonitrile (or ethers thereof) at a reasonable cost.

SUMMARY OF THE INVENTION

The present invention includes a method of preparing a substituted benzonitrile represented by Structural Formula (I):

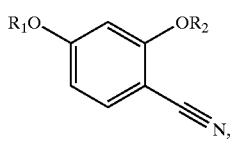

(I)

where $R_1$ and $R_2$ are each independently —H, a substituted or unsubstituted alkyl group, or a substituted or unsubstituted aryl group;
comprising the steps of:
a.) amidating a substituted benzoic acid represented by Structural Formula (II):

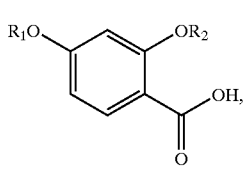

(II)

where $R_1$ and $R_2$ are as defined above; by reacting the substituted benzoic acid with an activating agent and an α,β-aminoalcohol represented by Structural Formula (III):

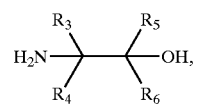

(III)

where $R_3$, $R_4$, $R_5$, and $R_6$ are each —H or substituted or unsubstituted alkyl groups, thereby forming a substituted 2-phenyloxazoline represented by Structural Formula (IV):

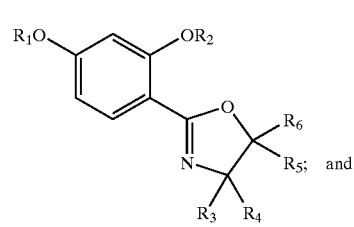

(IV)

b.) reacting the substituted 2-phenyloxazoline with phosphorus oxychloride, thereby forming the substituted benzonitrile represented by Structural Formula (I).

The present invention also includes a method of preparing a substituted benzonitrile represented by Structural Formula (V):

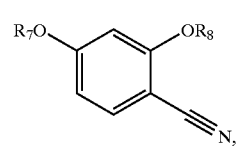

(V)

where $R_7$ and $R_8$ are each —H or a substituted or unsubstituted aryl group; comprising the steps of:
a.) protecting hydroxyl groups of 2,4-dihydroxybenzoic acid with one or more substituted or unsubstituted arylalkyl protecting groups, thereby forming a protected 2,4-dihydroxybenzoic acid;
b.) amidating the protected 2,4-dihydroxybenzoic acid, by reacting the protected 2,4-dihydroxybenzoic acid with an activating agent and an α,β-aminoalcohol represented by Structural Formula (VI):

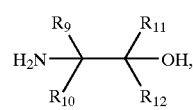

(VI)

where $R_9$, $R_{10}$, $R_{11}$, and $R_{12}$ are each —H or substituted or unsubstituted alkyl groups, thereby forming a substituted 2-phenyloxazoline represented by Structural Formula (VII):

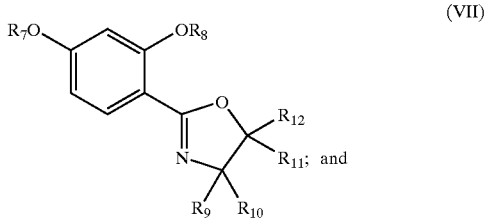

c.) reacting the substituted 2-phenyloxazoline with phosphorus oxychloride, thereby forming the substituted benzonitrile represented by Structural Formula (V).

In another embodiment, the present invention provides a method of preparing a compound represented by Structural Formula (VIII):

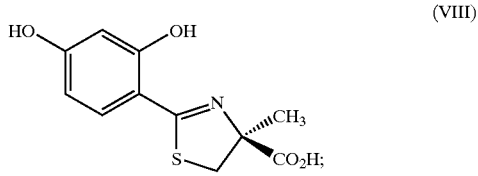

comprising the steps of:

a.) amidating a substituted benzoic acid represented by Structural Formula (II):

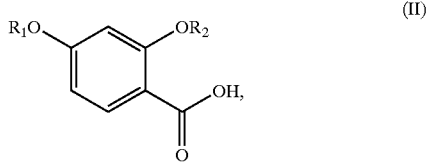

where $R_1$ and $R_2$ are each independently —H, a substituted or unsubstituted alkyl group, or a substituted or unsubstituted aryl group; by reacting the substituted benzoic acid with an activating agent and an α,β-aminoalcohol represented by Structural Formula (III):

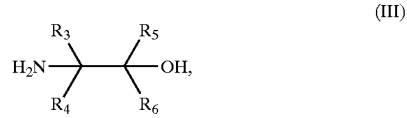

where $R_3$, $R_4$, $R_5$, and $R_6$ are each —H or substituted or unsubstituted alkyl groups, thereby forming a substituted 2-phenyloxazoline represented by Structural Formula (IV):

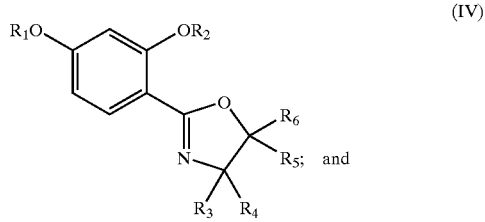

b.) reacting the substituted 2-phenyloxazoline with phosphorus oxychloride, thereby forming a substituted benzonitrile;

c.) if $R_1$ and $R_2$ are not each —H, cleaving ether groups in the product of step (b.), thereby forming 2,4-dihydroxybenzonitrile; and d.) coupling (S)-2-methylcysteine with 2,4-dihydroxybenzonitrile, thereby forming the compound represented by Structural Formula (VIII).

Advantages of the present invention include the facile synthesis of 2,4-dihydroxybenzonitrile, or an ether or diether thereof, from 2,4-dihydroxybenzoic acid, an inexpensive and readily available starting material. 2,4-Dihydroxybenzonitrile prepared by the method of the present invention can be coupled to (S)-2-methylcysteine to form 4'-hydroxydesazadesferrithiocin, also referred to as 4,5-dihydro-2-(2,4-dihydroxyphenyl)-4-methylthiazole-4(S)-carboxylic acid, an iron chelating agent.

DETAILED DESCRIPTION OF THE INVENTION

A useful and efficient method of preparing 2,4-dihydroxybenzonitrile, or an ether or diether thereof, involves reacting 2,4-dihydroxybenzoic acid (or an ether or diether thereof) with an α,β-aminoalcohol to form a 2-(2',4'-dihydroxyphenyl)-oxazoline (or an ether or diether thereof). The 2-(2',4'-dihydroxyphenyl)-oxazoline can subsequently be reacted with phosphorus oxychloride to obtain 2,4-dihydroxybenzonitrile or a related compound. For ethers and diethers of 2,4-dihydroxybenzonitrile, additional steps may be desirable to cleave the ether moieties and obtain 2,4-dihydroxybenzonitrile.

In one example, it is desirable to protect one, or preferably, both of the hydroxyl groups of 2,4-dihydroxybenzoic acid before proceeding with the conversion to 2,4-dihydroxybenzonitrile. A preferred protecting group is a substituted or unsubstituted arylalkyl group such as a benzyl group. Protecting groups can be added, for example, by reacting 2,4-dihydroxybenzoic acid, a base, and a benzyl compound having a leaving group (e.g., benzyl tosylate, a benzyl halide such as benzyl chloride or benzyl bromide) in a polar solvent and refluxing the mixture for several hours, typically 1 or more hours, 1 to 12 hours, 2 to 8 hours, or 3 to 6 hours. The amount of the benzyl compound depends, in part, on the number of hydroxyl groups to be protected and is generally one or more (e.g., to protect one hydroxyl group) or two or more equivalents, such as about 1 to about 10 equivalents, about 2 to about 8 equivalents, or about 3 to about 5 equivalents. The reaction temperature typically depends on the solvent, and is selected such that the reaction mixture refluxes at the chosen temperature(s), which is generally at or greater than room temperature. Suitable solvents in the present reaction are typically polar, aprotic solvents such as acetone, tetrahydrofuran, dimethylformamide, acetonitrile, ethyl acetate, ethyl ether, dioxane, and hexamethylphosphoramide. Suitable bases for the present reaction typically include alkali metal and alkaline earth metal hydroxides, alkoxides, and carbonates, including sodium hydroxide, sodium methoxide, sodium ethoxide, sodium carbonate, potassium hydroxide, potassium methoxide, potassium ethoxide, cesium carbonate, calcium carbonate, and potassium carbonate.

It may be advantageous to protect both the hydroxyl groups and the carboxylic acid of 2,4-dihydroxybenzoic acid, and the carboxylic acid can be protected before, simultaneously with or after the hydroxyl groups. The fully protected product is generally a solid, and can be filtered and concentrated by suitable methods.

In order to deprotect the carboxylic acid moiety, the solid can be reacted at, for example, room temperature or greater (e.g., 20–100° C., 25–80° C., 30–60° C., 35–50° C.) with a base, such as those listed above, and a polar, protic solvent (e.g., methanol, ethanol, propanol, isopropanol, water, formamide, dimethylformamide, N-ethylacetamide, formaldehyde diethyl acetal) for several hours (e.g. one or more hours, 1–12 hours, 2–10 hours, 3–8 hours, 4–6 hours). The amount of base can be catalytic or stoichiometric, but is preferably stoichiometric, such that there are one or more equivalents (e.g., about 1 to about 10 equivalents, about 2 to about 8 equivalents, about 3 to about 6 equivalents) of base. The deprotected carboxylate acid (carboxylate) moiety can be neutralized with an excess of a dilute acid such as hydrochloric acid, hydrobromic acid, nitric acid, or sulfuric acid. The neutralized acid often forms a solid, where only the hydroxyl groups of 2,4-dihydroxybenzoic acid are protected. This solid can be filtered and optionally recrystallized from a solvent mixture, such as a methanol-chloroform mixture.

In the next step of the reaction, either 2,4-dihydroxybenzoic acid or one of the protected species described above can be reacted with an activating agent such as a chlorinating agent, for example oxalyl chloride, phosphorus trichloride, or preferably thionyl chloride, in a nonpolar solvent such as pentane, heptane, octane, hexane(s), cyclohexane, carbon tetrachloride, toluene, xylenes, or preferably benzene, to form an acid chloride. The acid chloride can be dissolved in a polar, aprotic solvent such as those listed above, and optionally cooled below room temperature (e.g., about 15° C. to about −35° C., about 10° C. to about −20° C., 5° C. to about −5° C.). Then, an α,β-aminoalcohol can be added, followed by a base. Alternatively, 2,4-dihydroxybenzoic acid or the protected species described above can be reacted with an activating agent such as hydroxybenzotriazole (HOBt), imidazole, or 1,3-dicyclohexylcarbodiimide (DCC) and an α,β-aminoalcohol to produce an N-hydroxyethylamide. α,β-Aminoalcohols are typically represented by Structural Formula (III) or Structural Formula (VI):

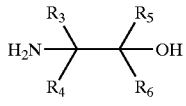

(III)

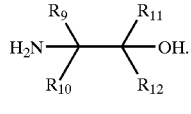

(VI)

Preferably, $R_3$, $R_4$, $R_9$, and $R_{10}$ are each independently an unsubstituted alkyl group, such as methyl, ethyl, propyl, isopropyl, butyl, isobutyl, or t-butyl, and $R_5$, $R_6$, $R_{11}$, and $R_{12}$ are each —H. Even more preferably, $R_3$, $R_4$, $R_9$, and $R_{10}$ are each methyl. Suitable bases include dialkylamines and trialkylamines, preferably dimethylamine, diethylamine, diphenylamine, triphenylamine, trimethylamine, diisopropylamine, diisopropylethylamine, 1,4-diazabicyclo[2.2.2]octane (DABCO), 1,5-diazabicyclo[4.3.0]non-5-ene (DBN), or triethylamine. The mixture of acid chloride and α,β-aminoalcohol are typically stirred at, for example, room temperature or greater, for at least about 15 minutes. Typically, the reaction continues for 15 minutes to 6 hours, 30 minutes to 3 hours, 45 minutes to 2 hours, or 60 to 90 minutes. After a desired amount of time, the mixture can be washed with an aqueous basic salt solution such as sodium hydroxide, potassium hydroxide, sodium carbonate, potassium carbonate, sodium bicarbonate, or potassium bicarbonate, and subsequently dried over a hydroscopic substance such as potassium carbonate, sodium carbonate, potassium sulfate, or sodium sulfate, and concentrated. The product of this step is an N-hydroxyethylamide.

The N-hydroxyethylamide and one or more equivalents of an activating agent such as thionyl chloride (e.g, about 1 to about 10 equivalents, about 2 to about 8 equivalents, about 3 to about 6 equivalents) are generally stirred for at least 10 minutes (e.g., 10 minutes to 200 minutes, 20 minutes to 100 minutes, 30 minutes to 50 minutes) at, for example, about 0° C. to about 90° C., about 10° C. to about 60° C., about 15° C. to about 40° C., or about 20° C. to about 30° C. The mixture of N-hydroxyethylamide and thionyl chloride is neutralized with an aqueous base such as potassium hydroxide, sodium hydroxide, potassium carbonate, sodium carbonate, potassium bicarbonate, or sodium bicarbonate. The mixture can then be extracted with a polar, aprotic solvent, as listed above, and washed with water. The mixture can be dried over a hydroscopic substance and concentrated to obtain a 2-aryloxazoline.

A mixture of the 2-aryloxazoline, an organic base, and phosphorus oxychloride are typically heated together. Suitable organic bases include piperidine, pyrrolidine, and preferably pyridine, which are present in a stoichiometric or a catalytic amount. When the above mixture is heated, the temperature is generally 60° C. or greater, such as about 60° C. to about 150° C., about 70° C. to about 130° C., about 80° C. to about 120° C., or about 90° C. to about 110° C. Preferably, the above mixture is heated for at least about 30 minutes, such as about 30 minutes to about 6 hours, about 1 hour to about 4 hours, or about 2 hours to about 3 hours. The mixture can be cooled to about room temperature (e.g., about 20° C. to about 40° C. or about 20° C. to about 30° C.), and then ice-cold water can be added. The mixture can be extracted with a polar, aprotic solvent, preferably ethyl acetate. The extracted mixture can be washed with a basic aqueous salt solution, preferably a sodium bicarbonate or potassium bicarbonate solution, before water is evaporated to give either 2,4-dihydroxybenzonitrile or the protected form, 2,4-dibenzyloxybenzonitrile.

In one embodiment, protecting groups of 2,4-dihydroxybenzonitrile are cleaved. The protecting groups are typically bonded to 2,4-dihydroxybenzonitrile through an ether linkage (e.g., 2,4-dibenzyloxybenzonitrile). Ether linkages can be cleaved, for example, by methods described on pages 433–434 and 1012–1014 of "Advanced Organic Chemistry, Fourth Edition," by Jerry March, Wiley-Interscience, 1992 and references therein, all of which are incorporated by reference. Typically, ether linkages are cleaved by reaction with a mineral acid (e.g, HBr, HI) or a Lewis acid. Suitable Lewis acids include $BF_3$, $BCl_3$, $(CH_3)_2BBr$, $BBr_3$, $AlCl_3$, $(CH_3)_3SiI$, $SiCl_4/NaI$, $SiH_2I_2$, LiI, $NaI/BF_3$, and $(CH_3)_3SiCl/NaI$.

Cysteine or a 2-alkylcysteine such as (S)-2-methylcysteine can be coupled with 2,4-dihydroxybenzonitrile, or an ether or diether thereof. Cysteine and related compounds can also be coupled with other substituted and unsubstituted aryl nitriles. In a preferred embodiment, (S)-2-methylcysteine is coupled to 2,4-dihydroxybenzonitrile to form 4,5-dihydro-2-(2,4-dihydroxyphenyl)-4-methylthiazole-4(S)-carboxylic acid (also known as 4'-hydroxydesazadesferrithiocin).

Syntheses of cysteine and cysteine derivatives suitable for coupling can be found in U.S. application Ser. Nos. 60/381,012, 60/381,021, 60/380,894, 60/380,910, 60/380,880, 60/381,017, 60/380,895 and 60/380,903, filed May 15, 2002, and U.S. application Ser. No. 60/392,833, filed Jun. 27, 2002; the entire teachings of which are incorporated herein by reference.

Typically, coupling of cysteine or a 2-alkylcysteine and a substituted benzonitrile includes converting the benzonitrile into a benzimidate. The benzimidate can be formed, for example, by reacting the benzonitrile with an alcohol such as methanol, ethanol, n-propanol, or isopropanol in the presence of an acid such as hydrochloric acid. The benzimidate is then reacted with the cysteine (or related compound) under basic conditions. Acceptable bases include trimethylamine, triethylamine, triphenylamine, diisopropylamine, diisopropylethylamine, diethylamine, dimethylamine, DABCO, DBN, and the like. The reaction between the benzimidate and the cysteine results in the thiazoline (or 4,5-dihydrothiazole) containing product. When forming the benzimidate from a hydroxylated benzonitrile (e.g., 2,4-dihydroxybenzonitrile), the hydroxyl groups are advantageously protected (e.g., with a substituted or unsubstituted alkyl or arylalkyl group such as a benzyl group). The protecting groups are subsequently cleaved, typically by catalytic hydrogenation.

Products of the above methods can be purified by methods known in the art, such as emulsion crystallization.

The methods of the claimed invention can be used to manufacture other related desferrithiocin analogs and derivatives. Examples of such analogs include those described in U.S. Pat. Nos. 5,840,739, 6,083,966, 6,159,983, 6,521,652 and 6,525,080 to Raymond J. Bergeron, Jr., the contents of which are incorporated herein by reference. Additional examples can be found in PCT/US93/10936, PCT/US97/04666, and PCT/US99/19691, the contents of which are incorporated by reference.

An alkyl group is a hydrocarbon in a molecule that is bonded to one other group in the molecule through a single covalent bond from one of its carbon atoms. Alkyl groups can be cyclic or acyclic, branched or unbranched, and saturated or unsaturated. Typically, an alkyl group has one to about 24 carbons atoms, or one to about 12 carbon atoms. Lower alkyl groups have one to four carbon atoms and include methyl, ethyl, n-propyl, iso-propyl, n-butyl, sec-butyl and tert-butyl.

Aromatic (or aryl) groups include carbocyclic aromatic groups such as phenyl, p-tolyl, 1-naphthyl, 2-naphthyl, 1-anthracyl and 2-anthracyl. Aromatic groups also include heteroaromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aromatic groups also include fused polycyclic aromatic ring systems in which a carbocyclic, alicyclic, or aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, and 3-isoindolyl, 1-isoquinolinyl, 3-quinolinyl, 1-isoindolyl, and 3-isoindolyl.

Suitable substituents for alkyl groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aryl group. Aryl groups can additionally be substituted by an alkyl or cycloaliphatic group (e.g. an aryl group can be substituted with an alkyl group to form an alkylaryl group such as tolyl). A substituted aryl group can have more than one substituent.

Suitable substituents for aryl groups include —OH, halogen, (—Br, —Cl, —I) and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), and guanidine. Each R' is independently an alkyl group or an aryl group. Aryl groups can additionally be substituted by an alkyl or cycloaliphatic group (e.g. an aryl group can be substituted with an alkyl group to form an alkylaryl group such as tolyl). A substituted aryl group can have more than one substituent.

Exemplification

EXAMPLE 1

Synthesis of 2,4-Benzyloxybenzonitrile

A. 2,4-Dibenzyloxy Benzoic Acid

A solution of 2,4-dihydroxybenzoic acid (5 g), anhydrous K$_2$CO$_3$ (40 g) and benzyl bromide (16 mL) in acetone (100 mL) was refluxed for 4 hours. After filtration of solid, the filtrate was concentrated. The residue was stirred at room temperature with KOH (6 g), and methanol (20 mL) for 4 hours, and neutralized with dilute HCl (pH 2). The solid thus formed was filtered and recrystallized from a methanol-chloroform mixture (3:1) to get 3.5 g of the product. Concentration of mother liquor gave an additional 1 g of the product.

B. Preparation of Oxazoline

The suspension of the acid from Part A (3.2 g), SOCl$_2$ (2 mL) in dry benzene (10 mL) was heated at reflux for 8 hours, concentrated and co-distilled with benzene. The resulting acid chloride was dissolved in CH$_2$Cl$_2$ (8 mL), cooled in ice water and then 2-amino-2-methylpropanol (2.2 g) was added, followed by triethylamine (1.4 mL). The resulting mixture was stirred at room temperature for 1 hour and washed with a sodium bicarbonate solution, water, dried over K$_2$CO$_3$ and concentrated to give an amide (3.3 g) as a solid.

The above amide (1 g) and SOCl$_2$ (1 mL) were stirred at room temperature for 0.5 hours, neutralized with 20% aqueous NaOH. The reaction mixture was extracted with CHCl$_3$, washed with water, and dried over K$_2$CO$_3$ and concentrated to give an oxazoline (0.88 g) as a solid.

C. Preparation of 2,4-Dibenzyloxy Benzonitrile

The oxazoline (0.75 g), pyridine (2 mL) and POCl$_3$ (1 mL) were heated at 90° C. for 2 hours, cooled to room temperature, and decomposed with ice cold water and extracted with ethyl acetate. The organic layer was washed with saturated sodium bicarbonate, and the water was evaporated to give 2,4-dibenzyloxybenzonitrile (0.45 g) as a solid.

EXAMPLE 2

35 mg of R- and S-4,5-dihydro-2-(2,4-dihydroxyphenyl)-4-methylthiazole-4-carboxylic acid were dissolved in 1 ml of a mixture of 9% N-methyl-pyrrolidone, 9% v/v 2-hexanol, 10% v/v Rhodafac RE 610, 5% v/v Soprophor FL and 68% v/v water by heating to 50° C. in a 5 mL vial. After the product was completely dissolved, the microemulsion was cooled down to room temperature and agitated with a shaking machine (350 rpm). During two hours, no spontaneous crystallisation was observed. The mixture was then seeded with two drops of a dilute, finely ground suspension of pure S-product crystals grown under similar conditions. After two hours of shaking, the resulting crystals were filtered off, washed with water and dried in a gentle nitrogen stream. The procedure yielded 5.4 mg (15.4%) of colorless crystals, with a greater than 90% purity of the S entantiomer.

EXAMPLE 3

4.00 g (S)-2-methylcysteine hydrochloride (23.3 mmol, 1.0 meq) and 3.14 g 2,4-dihydroxy benzonitrile (23.3 mmol, 1.0 meq) were suspended in 40 mL ethanol. After degassing this mixture with nitrogen (30 min) 4.95 g triethylamine (6.8 mL, 48.9 mmol, 2.05 meq) were added. The obtained suspension was heated under reflux in an atmosphere of nitrogen for 20 hours and then cooled to room temperature. From this suspension ethanol was evaporated under reduced pressure until an oil (20% of the initial volume) was obtained. This oil was dissolved in 50 mL water. The solution was adjusted to pH 7.5 with 1.20 ml 20% KOH and was extracted two times each with 20 mL methyl t-butyl ether (MTBE). The aqueous layer was separated, adjusted with 20% KOH to pH 11 and again extracted two times each with 20 mL MTBE. After separating the aqueous layer the pH was set with concentrated HCl to 7.5 and traces of MTBE were distilled off. Then the aqueous solution was acidified with 1.50 mL concentrated HCl to pH 1.5. The product precipitated. This suspension was stirred at 4° C. for 1 hour. Then the precipitate was filtered, washed two times each with 10 mL water (5° C.) and dried at 45° C. under vacuum. The reaction yielded 5.17 g (87.6%) of crude 4,5-dihydro-2-(2,4-dihydroxyphenyl)-4-methylthiazole-4 (S)-carboxylic acid product. $^1$H-NMR showed no significant impurity.

EXAMPLE 4

2,4-Dibenzyloxybenzonitrile (0.121 mol) was dissolved in 5.85 g (0.127 mol) ethanol and 19.4 ml 1,2-dimethoxyethane in a double walled reactor. This solution was cooled to −5° C., stirred and saturated with dry HCl gas over 5 hours at 0–3° C. The reaction mixture was stirred overnight at 2–4° C. under nitrogen. During this time, a product crystallized. The white crystals were filtered off, washed with 1,2-dimethoxyethane (5° C., three times each with 13 ml) and dried. A total of 30 of the protected ethyl benzimidate was isolated (Yield 88.4%, purity 98.9%).

The protected ethyl benzimidate described above was dissolved in methanol to generate a 10% solution and was catalytically hydrogenated at room temperature using 5% Pd/C as a catalyst. The reaction was completed after 8 hours. The solution was filtered and the solvent evaporated to yield the deprotected product as an orange-yellow solid. The reaction yielded 19.6 g (94%) of product.

In contrast, the formation of the imidate with 2,4 dihydroxybenzonitrile was a low yielding process, generating the desired product in only 20% yield and with less than desired purity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preparing a substituted benzonitrile represented by Structural Formula (I):

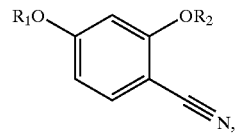

(I)

wherein $R_1$ and $R_2$ are each independently —H, a substituted or unsubstituted alkyl group, or a substituted or unsubstituted aryl group;
comprising the steps of:
a.) amidating a substituted benzoic acid represented by Structural Formula (II):

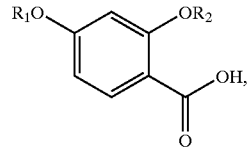

(II)

wherein $R_1$ and $R_2$ are as defined above; by reacting said substituted benzoic acid with an activating agent and an α,β-aminoalcohol represented by Structural Formula (III):

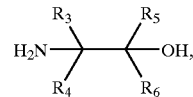

(III)

wherein $R_3$, $R_4$, $R_5$, and $R_6$ are each —H or substituted or unsubstituted alkyl groups, thereby forming a substituted 2-phenyloxazoline represented by Structural Formula (IV):

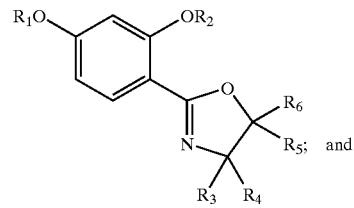

(IV)

b.) reacting the substituted 2-phenyloxazoline with phosphorus oxychloride, thereby forming the substituted benzonitrile represented by Structural Formula (I).

2. The method of claim 1, wherein $R_3$ and $R_4$ are each independently an unsubstituted alkyl group, and $R_5$ and $R_6$ are each —H.

3. The method of claim 2, wherein $R_1$ and $R_2$ are each benzyl.

4. The method of claim 3, wherein $R_3$ and $R_4$ are each methyl.

5. The method of claim 1, further comprising the step of preparing the substituting benzoic acid from 2,4-dihydroxybenzoic acid and a benzyl halide or benzyl tosylate.

6. The method of claim 2, wherein $R_1$ and $R_2$ are each —H.

7. The method of claim 6, wherein $R_3$ and $R_4$ are each methyl.

8. A method of preparing a substituted benzonitrile represented by Structural Formula (V):

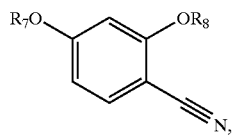

wherein $R_7$ and $R_8$ are each —H or a substituted or unsubstituted aryl group;

comprising the steps of:

a.) protecting hydroxyl groups of 2,4-dihydroxybenzoic acid with one or more substituted or unsubstituted arylalkyl protecting groups, thereby forming a protected 2,4-dihydroxybenzoic acid;

b.) amidating the protected 2,4-dihydroxybenzoic acid, by reacting said protected 2,4-dihydroxybenzoic acid with an activating agent and an α,β-aminoalcohol represented by Structural Formula (VI):

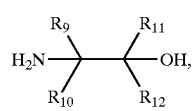

wherein $R_9$, $R_{10}$, $R_{11}$, and $R_{12}$ are each —H or substituted or unsubstituted alkyl groups, thereby forming a substituted 2-phenyloxazoline represented by Structural Formula (VII):

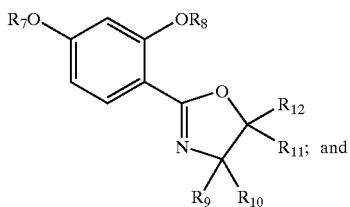

c.) reacting the substituted 2-phenyloxazoline with phosphorus oxychloride, thereby forming the substituted benzonitrile represented by Structural Formula (V).

9. The method of claim 8, wherein $R_9$ and $R_{10}$ are each independently an unsubstituted alkyl group and $R_{11}$ and $R_{12}$ are each —H.

10. The method of claim 9, wherein $R_9$ and $R_{10}$ are each methyl.

11. The method of claim 10, wherein the protecting groups are benzyl groups.

12. The method of claim 11, further comprising the step of cleaving the protecting groups from product of step (c.), thereby forming 2,4-dihydroxybenzonitrile.

13. A method of preparing a compound represented by Structural Formula (VIII):

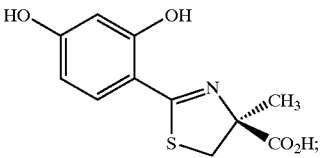

comprising the steps of:

a.) amidating a substituted benzoic acid represented by Structural Formula (II):

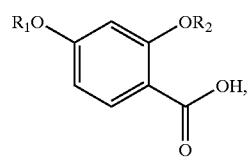

wherein $R_1$ and $R_2$ are each independently —H, a substituted or unsubstituted alkyl group, or a substituted or unsubstituted aryl group; by reacting said substituted benzoic acid with an activating agent and an α,β-aminoalcohol represented by Structural Formula (III):

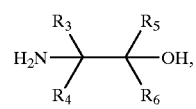

wherein $R_3$, $R_4$, $R_5$, and $R_6$ are each —H or substituted or unsubstituted alkyl groups, thereby forming a substituted 2-phenyloxazoline represented by Structural Formula (IV):

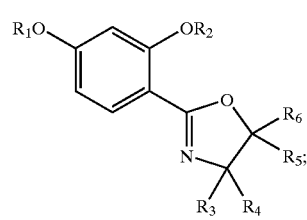

b.) reacting the substituted 2-phenyloxazoline with phosphorus oxychloride, thereby forming a substituted benzonitrile;

c.) if $R_1$ and $R_2$ are not each —H, cleaving ether groups in the product of step (b.), thereby forming 2,4-dihydroxybenzonitrile; and d.) coupling (S)-2-methylcysteine with 2,4-dihydroxybenzonitrile, thereby forming the compound represented by Structural Formula (VIII).

* * * * *